United States Patent [19]

Bresler

[11] 4,416,289

[45] Nov. 22, 1983

[54] CIRCUITS FOR DETERMINING VERY ACCURATELY THE POSITION OF A DEVICE INSIDE BIOLOGICAL TISSUE

[75] Inventor: Robert G. Bresler, Watertown, Mass.

[73] Assignee: McCormick Laboratories, Inc., Acton, Mass.

[21] Appl. No.: 371,078

[22] Filed: Apr. 26, 1982

Related U.S. Application Data

[63] Continuation-in-part of Ser. No. 261,521, May 7, 1981.

[51] Int. Cl.³ .......................... A61B 5/05; A61B 5/06
[52] U.S. Cl. .................................. 128/737; 128/1.5; 128/207.14; 324/243; 340/551
[58] Field of Search .................. 128/737, 207.14, 1.3, 128/1.5; 324/233, 443, 243; 340/551

[56] References Cited

U.S. PATENT DOCUMENTS

| | | | |
|---|---|---|---|
| 2,442,805 | 6/1948 | Gilson | 128/737 X |
| 3,371,272 | 2/1968 | Stanton | 128/1.5 X |
| 3,436,649 | 4/1969 | Takechi et al. | 324/243 |
| 3,460,528 | 8/1969 | Carney | 128/737 X |
| 3,826,973 | 7/1974 | Pflaum | 324/233 X |

OTHER PUBLICATIONS

Cullen et al., "A New Method of Positioning Endotracheal Tubes," *Anesthesiology*, vol. 43, No. 5, Nov. 1975, pp. 596-599.

*Primary Examiner*—Henry J. Recla
*Assistant Examiner*—John C. Hanley

[57] ABSTRACT

A circuit for determining very accurately the position of a device inside biological tissue in which a probe generates a small magnetic field which can be disturbed by a magnetically permeable metal in the device inside the tissue when a narrow end of the probe is positioned immediately adjacent to tissue containing the metal, whereby after the metal-carrying device is inserted in the tissue, the end of the probe is used to precisely locate the device by scanning the tissue until the magnetic field is disturbed, which disturbance causes the circuit to generate a signal.

14 Claims, 6 Drawing Figures

CIRCUITS FOR DETERMINING VERY ACCURATELY THE POSITION OF A DEVICE INSIDE BIOLOGICAL TISSUE

Cross-Reference to Other Applications

This application is a continuation-in-part of my U.S. Patent Application Ser. No. 261,521, filed May 7, 1981, hereby incorporated by reference.

FIELD OF THE INVENTION

This invention relates to a circuit for an apparatus for determining accurately the position of a device inside biological tissue, particularly the position of an endotracheal tube in the trachea or windpipe of a medical patient.

BACKGROUND OF THE INVENTION

It is necessary to insure that the breathing passageway of certain medical patients, e.g., those in surgery or intensive care, is kept open at all times. This is accomplished in the prior art by means of an endotracheal tube which is inserted through the patient's mouth or nose and extends through the patient's throat and into the patient's windpipe is trachea. These prior art tubes are hollow and open at both ends, and the end that extends outside the mouth or nose is anchored in place, usually with tape. Air can then pass through the tube into and out of the patient's lungs.

The principal drawback of the prior art tubes is that the distal end of the tube inside the patient must be inserted to and kept at a relatively specific position which is at about the midpoint of the trachea. This is because if the tube is inserted too far into the trachea, its distal end may extend into the bronchial tree for one lung, and thus the other lung will receive no air and may collapse. On the other hand, if the end of the tube is not inserted far enough, it may interfere with the vocal cords, or it may enter the esophagus, which opens near the bottom of the throat, and air would not reach the lungs. In a normal adult the trachea is about 11 centimeters in length, and the distal end of the tube is generally positioned at the trachea's approximate midpoint. This positioning, however, has much less margin for error in children or infants, whose tracheas are much shorter in length. Furthermore, for both adults and children, even if the tube is properly positioned initially, the movements of the patient often cause the tube to move up or down, and therefore the location of the distal end of the tube must be continuously monitored.

The prior art uses several methods for monitoring tube position. First, the tube position can be determined by X-ray, but notwithstanding the possible adverse effect of continued exposure to X-rays, the principal drawback here is that by the time the X-ray is taken, developed and returned, the tube may have moved again. Accordingly, two real-time monitoring methods are in wide use. They involve listening to the chest to hear if both lungs are filling and visual observation of the depth markings on the exposed tube. Neither of these real-time methods, however, is very precise.

SUMMARY OF THE INVENTION

I have discovered a circuit for an apparatus for determining very accurately the position of a device inside biological tissue, particularly the position of an endotracheal tube in the trachea of a patient. The apparatus comprises a detecting instrument which includes my circuit for generating a magnetic field, which when disturbed causes the circuit to generate a signal. In the preferred embodiment, the field is disturbed by the presence of a highly magnetically permeable metal attached to the device inserted into the tissue.

In a preferred embodiment, the probe has a central coil and two end coils, all identical. When the instrument is turned on, the central coil is activated thereby setting up a magnetic field, and the voltage outputs from the two end coils are composed by the circuit. If the end of the probe comes adjacent to the metal attached to the device in the tissue, there is an imbalance in the field, and the circuit generates a signal. At that point, the position of the probe on the skin is recorded on the patient's skin.

DESCRIPTION OF THE PREFERRED EMBODIMENTS

DRAWINGS

I now turn to a description of the preferred embodiments, after first briefly describing the drawings.

STRUCTURE

Figures 1, 3:
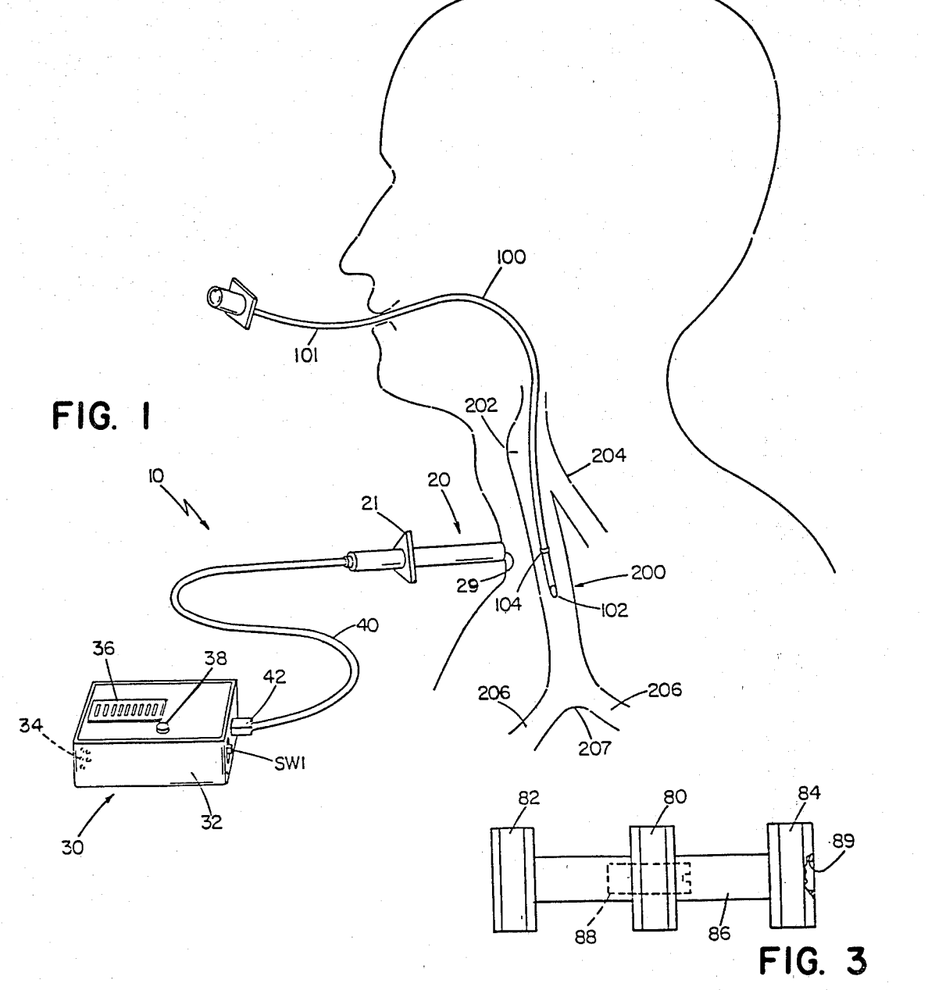
FIG. 1 is a side view in partial section of the invention along with the endotracheal tube in place in a patient.
FIG. 3 is an enlarged sectional view of a coil arrangement of the invention.

Referring to FIG. 1, a locating apparatus is shown at 10. Locating apparatus 10 generally comprises a probe 20 and a detector instrument 30, attached together by a flexible electrical cable 40.

Figure 2:
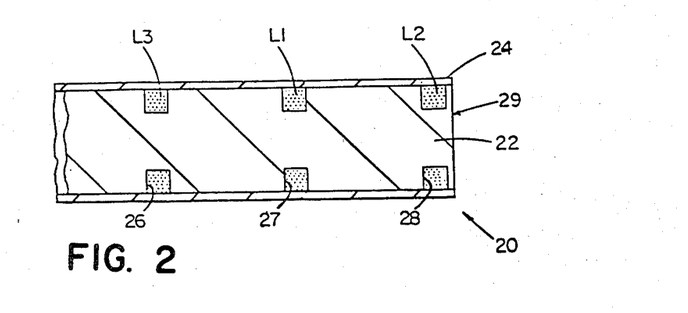
FIG. 2 is an enlarged sectional view of the probe of this invention.

Probe 20 generally comprises three coils L1, L2 and L3 co-axially wound around a core 22 which is disposed inside a cylindrical casing 24, which is shaped to act as a pointer. The core 22 has three annular grooves 26, 27, 28 in which the coils L3, L1 and L2, each containing the same number of windings, are located. However, coils with different numbers of windings may also be used. The end grooves 26, 28 are equidistantly spaced from the central groove 27. In the preferred embodiment, the distance between grooves is about 1 cm, and the grooves are each about 2 mm wide and 2 mm deep. The core itself has a diameter of about 9 mm. Separate pairs of leads (not shown) are connected to each coil, and the leads are carried to the detector instrument 30 by cable 40. The front end 29 of the probe 20 is opposite the cable end, and a slide 21 is movably disposed on the casing 24. Instead of the slide 21, the probe 20 may have a marking element attached to its front end 29. The end of the core 22 is set adjacent to the front end 29 of the casing 24, but it could be set at some distance inside the casing away from the front end 29. The casing is preferably made of a non-magnetic material such as plastic, while the core 22 is made of phenolic resin impregnated linen.

The detector instrument 30 generally comprises a box 32 which is of a size that can easily be held in one hand. The box 32 is a switch SW1 on its front end, a speaker opening 34 on its back end, and a series of lights 36 and a calibration control knob 38 on its top. Detector instrument 30 contains a circuit 50 for the probe 20, which circuit 50 is shown in FIG. 4.

The instrument 30 is detachable from the cable 40 at connector 42. This allows the probe 20 to be sterilized when needed, which sterilization process would otherwise damage the instrument 30 and its circuit 50. In addition, since the probe 20 is detachable, different sized probes for different types of patients, e.g., adults, infants, can be used with the same instrument 30.

Figure 4:
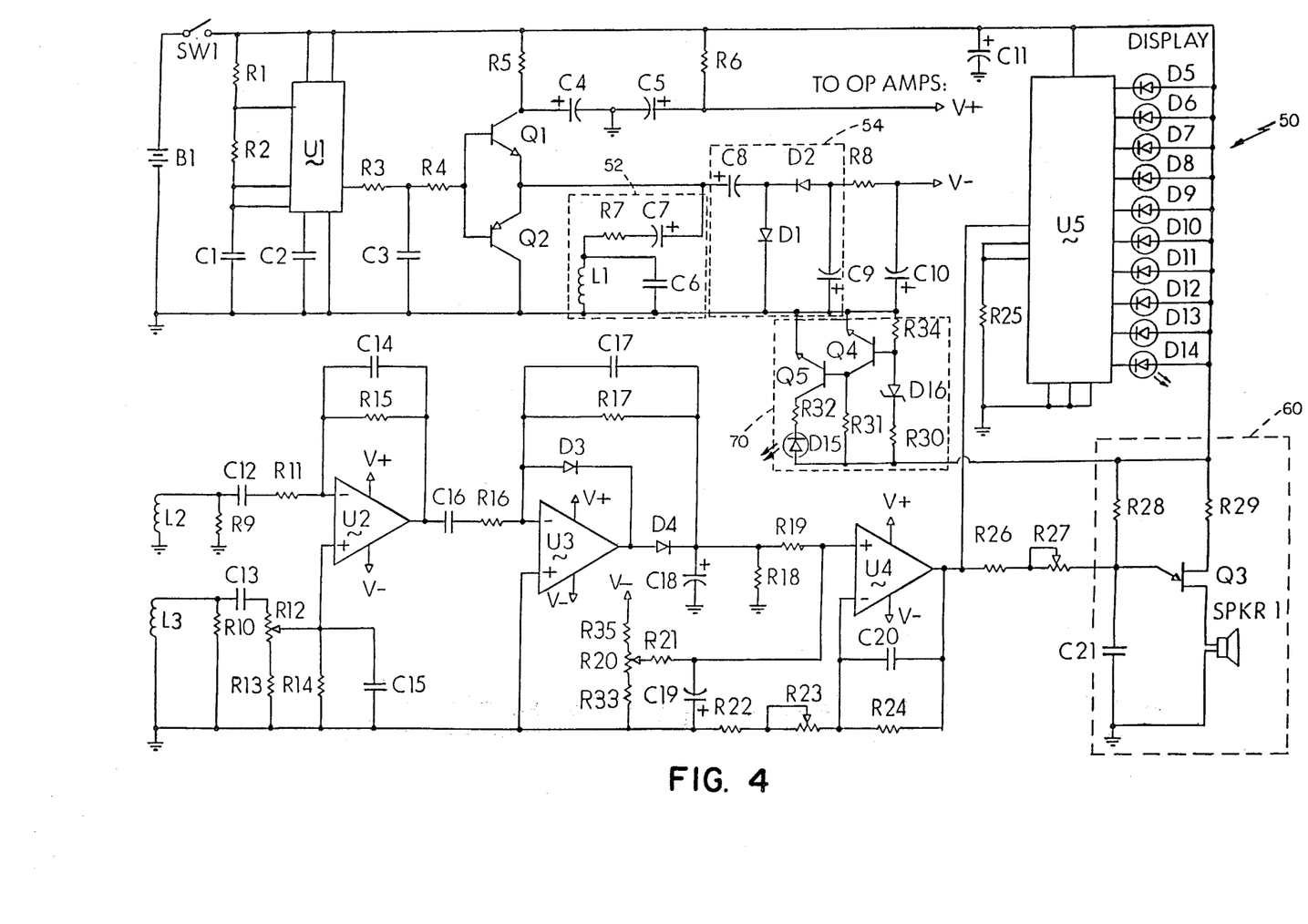
FIG. 4 is a schematic diagram of the circuit of this invention.

Referring to FIG. 4, the circuit 50 has a voltage source B1 connected between ground and the switch SW1, shown schematically. The voltage source B1 in the preferred embodiment is 12.6 volt mercury battery.

A multivibrator U1 is connected across the voltage source B1 and switch SW1. The duty cycle of the multivibrator U1 is set by resistors R1, R2 in series with C1. Capacitor C2 stabilizes a reference point in the multivibrator U1. In the preferred embodiment, multivibrator U1 is CMOS, and preferably an Intersil ICM7555. R1 is 10K ohms. R2 is 330K ohms, and C1 and C2 are 1000 picofarads and 0.01 microfarads respectively.

The output from multivibrator U1 is connected through resistors R3 and R4 to the bases of transistors Q1 and Q2. Capacitor C3 is connected to ground from between resistors R3 and R4. The transistors Q1 and Q2, which are NPN and PNP respectively, are arranged as an emitter-follower circuit. In the preferred embodiment, Q1 is a 2N2222A, and Q2 is a 2N2907A. Resistors R3 and R4 are 330 ohms and 220 ohms respectively, and capacitor C3 is 1000 picofarads.

The collector of transistor Q1 is connected through resistor R5, which is 22 ohms, to the positive side of the voltage source B1 (when switch SW1 is closed) and to ground through capacitor C4, which is 47 microfarads. Capacitor C5 and resistor R6 are connected to the positive side of voltage source B1. Capacitor C5 is also 47 microfarads, and resistor R6 is 100 ohms.

The emitters of transistors Q1, Q2 are connected to central coil circuit 52. Central coil circuit 52 comprises capacitor C7 in series with resistor R7 and central coil L1 of the probe 20. Capacitor C6 is connected across the coil L1. Capacitors C6 and C7 are 0.1 microfarad and 6.8 microfarads respectively and resistor R7 is 150 ohms.

The emitters of transistors Q1 and Q2 are also connected to voltage doubler circuit 54. Doubler circuit 54 is comprised of capacitors C8, C9 and diodes D1 and D2. Diodes D1 and D2 are both 1N4148, and capacitors C8 and C9 are both 47 microfarads. Also, a resistor R8 of 100 ohms and capacitor C10 of 47 microfarads in series are connected across capacitor C9.

The coil L1 is, as previously explained, the central or transmitting coil on the core 22 of the probe 20. Receiving coil L2 is the coil at the front end 29 of the probe 20 and receiving coil L3 is at the opposite end. As shown in the bottom portion of FIG. 4, coil L2 is connected through capacitor C12 and resistor R11 to the negative input of differential amplifier U2. This side of coil L2 is also connected to ground through terminating resistor R9.

The coil L3 is connected to the positive input of differential amplifier U2 through capacitor C13 and variable resistor R12. This input circuit for coil L3 also has a terminating resistor R10, and variable resistor R12 is connected to ground through resistor R13. Resistor R14 is connected from the wiper of the variable resistor R12 to ground, and capacitor C15 is in parallel with resistor R14. The feedback loop for amplifier U2 comprises the parallel combination of resistor R15 and capacitor C14.

The amplifier U2 is a Texas Instruments TL081. Terminating resistors R9, R10 are both 220 ohms. Capacitors C12 and C13 are both 0.1 microfarads. Resistor R11 is 1K ohms, and variable resistor R12 is 20K ohms. Resistors R13 and R14 are 220K ohms each, and capacitor C15 is 120 picofarads. The feedback loop resistor R15 and capacitor C14 are 220K ohms and 1000 picofarads.

The output of amplifier U2 is fed through capacitor C16 of 0.1 microfarad and R16 of 220 ohms to the negative input of amplifier U3, the positive input of which is tied to ground. Diode D3, a 1N4148, is connected between the output of amplifier U3 and its negative input. The feedback loop for the amplifier U3 comprises the parallel combination of resistor R17 and capacitor C17 connected to the negative input and the output of the amplifier U3 through diode D4, also a 1N4148. The amplifier U3 is a Texas Instruments TL082, and resistor R17 and capacitor C17 are 220K ohms and 0.047 microfarads.

The output from amplifier U3 is coupled to ground through capacitor C18 and resistor R18, 6.8 microfarads and 10K ohms. The output is also fed through R19 of 100K ohms to the positive input of non-inverting amplifier U4, which is also a Texas Instruments TL082. This positive input is also connected through resistors R21 to the wiper of variable resistor R20. Variable resistor R20 is connected between negative voltage V- and through resistor R33 to ground. Resistors R21, R20, R33, and R35 are 330K ohms, 20K ohms, 100K ohms, and 390K ohms, respectively.

The feedback loop for amplifier U4 which is connected between the negative input and its output comprises the parallel combination of capacitor C20 and resistor R24, 1 microfarad and 100K ohms, respectively, and includes resistors R22, R23. The negative input is also connected to ground through resistor R22 and potentiometer R23, being 1K ohms and 50K ohms, respectively.

The output from amplifier U4 is fed to display driver U5 which is connected to light emitting diodes D5 through D14, which comprise the lights 36 of detector instrument 30. Driver U5 is a National Semiconductor LM3915. Resistor R25 of 470 ohms is connected to the driver U5, and filter capacitor C11 of 47 microfarads is connected between the positive voltage line to the driver U5 and ground.

The output from amplifier U4 also is fed through resistor R26, potentiometer R27 to audio circuit 60. Audio circuit 60 comprises unijunction transistor Q3, a speaker, (shown schematically), capacitor 21 and resistors R28 and R29. The transistor Q3 is 2N1671. Resistors R26 and R27 ar 4.7K ohms and 20K ohms respectively. Resistors R28 and R29 are 4.7K ohms and 220 ohms, respectively, and capacitor C21 is 0.22 microfarads.

In the preferred embodiment, it is desirable to include a low battery voltage circuit 70. Circuit 70 comprises a pair of transistors Q4 and Q5, both TIS97. The base of Q4 is connected to ground through resistor R34 of 47K ohms and to the positive voltage through zener diode D16 and resistor R30. Resistor R30 is 820 ohms. The emitter of transistor Q4 is connected to ground, and its collector is connected to the base of transistor Q5 and resistor R31, the latter being 10K ohms and connected to the positive voltage source. The emitter of transistor Q5 is also connected to ground, and its collector is connected to the positive voltage source through resistor R32, of 820 ohms and light emitting diode D15.

OPERATION

The general operation of the invention is as follows. As shown in FIG. 1, an endotracheal tube 100 is inserted into a patient's mouth, and is extended down a desired distance into the trachea 200 in accordance with clinical judgment. The exposed portion of the tube 101 is fixed in place. It is desirable that the distal end 102 of the tube 100 is positioned at the approximate midpoint of the trachea 200, as shown, between the vocal cords 202 and the carina 207 of the bronchial tubes 206 to the lungs. The tube 100 has a band 104 of metal foil near its end, which band 104 is covered by plastic (not shown). The metal is preferably mu metal sheet (available from Arnold Engineering of Fullerton, California) or equivalent. The distance between the band 104 and the distal end 102 is selected so that for the particular type of patient, i.e., adult, child or infant, the band 104 will be positioned above the sternal manubrium notch (not shown) when the tube is in place.

In order to determine the positioning of the tube's distal end 102. the detector intrument 30 is turned on and this induces a current flow through the central coil L1 of the probe 20 thereby creating a magnetic field encompassing the receiving coils L2 and L3. As the coils L2 and L3 are balanced in terms of windings and distance from the central coil, any currents induced therein (in L2 and L3) will be the same. (This is not precisely correct due to the inherent minor manufacturing differences in coils intended to be identical).

The front end 29 of the probe 20 is then positioned perpendicular to the patient's throat area. When the probe end 29 is very near the metal band, which unbalances or distorts the magnetic field, the flux density through coil L2 will increase, and the currents through coils L2 and L3 will be unequal. This unequal current consequently causes the speaker to sound, and one of the light emitting diodes D5-14 to light. Due to the speaker sound, the operator can focus his attention on the patient and the probe and does not have to look at the instrument to determine if the band has been located. The frequency of the audible signal, and the diode lit depends upon the amount of voltage difference (e.g., the last diode D14 will light and the sound will be at the highest frequency when the probe is directly over the metal band).

The position of the band is then marked by sliding the slide 21 along the probe until it contacts the skin. The probe is removed while the slide is held in place on the skin. A pen is used to mark on the skin the location of the band through the probe opening (not shown) in the slide.

To monitor the position of the tube 100, the front end of the probe is placed on the marked spot. And if the maximum signal is not obtained, the tube has moved. The skin area is then scanned by passing the probe end over the surrounding area until the maximum reading is again obtained, and if necessary the tube is re-positioned so that it corresponds to the original or desired position. No reading (audible signal and lights) is obtained if the probe is more than just above the skin or on the skin more than a centimeter laterally away from the metal band. This is because the front receiving coil L2 has a small cross-sectional area and is relatively close to the transmit coil L1 and a relatively small field is used. As the receive coil L2 is small, the presence of the small metal band in the field will induce a substantial change in flux density through the coil L2. Also, as the coil L2 is circular, the resolution of the device is improved as a maximum signal is obtained when the band is adjacent to the center of the small coil L2.

The specific circuit operation is as follows. The switch SW1 is closed to turn on the instrument. Multivibrator U1 then produces an output which is a squarewave having a duty cycle of slightly more than 50%. The frequency of this signal is approximately 2KHz for the preferred embodiment.

The multivibrator U1 is CMOS so as to minimize the current it draws (about 100 microamps). Accordingly, its output current drive capability is not very high, and the emitter-followers, transistors Q1 and Q2, provide the necessary current gain (of about one hundred in the preferred embodiment). The interim circuit comprised of R3, R4 and C3 increases the rise and fall time of the transitional edges of the squarewaves so as to reduce switching noise. Resistor R5 and capacitor C4 decouple the transistor Q1 from the positive supply.

The output signal from the emitters of transistors Q1 and Q2 drives the coil circuit 52. Capacitor C7 a.c. couples the transistors' output (still a squarewave) through resistor R7 and through the central coil L1 thereby creating the magnetic field. Capacitor C6 of this circuit 52 damps some of the ringing due to the length of the cable between the probe and the detector instrument which houses the rest of the circuit 50 (except for the coils L1, L2 and L3).

The two other coils L2 and L3 are connected to differential amplifier U2 which amplifies the difference between voltages across the two coils L2 and L3. The outputs from the coils L2, L3 are unequal even in a no-metal-detected case due to the manufacturing tolerances of the coils of the preferred embodiment. As R15/R11 determines the gain, the gain of the preferred embodiment is 220. If the amplifier circuit, capacitor C14 defines the upper frequency of the bandpass of the amplifier U2.

As it is difficult to make coils L2 and L3 identical (as they are not, there will always be a small voltage difference between them) variable resistor R12 is used to correct out this error voltage so that the output voltage of amplifier U2 is nulled to a minimum output signal in a no-metal-detected condition. This can also be accomplished by mounting the coils so as to permit adjusting of the field relative to the receive coils. As shown in FIG. 3, for example, a transmit coil 80, receive coils 82, 84 are stationary, and mounted on hollow cylinder 86. Cylinder 86 is internally screw-threaded, and a metal slug 88 is movably mounted therein. The adjustment is made by inserting a screw driver through an opening 89 in the front end of the cylinder 86 and changing the axial position of the slug 88 with respect to the coils 80, 82, 84.

The output voltage of U2, which is the amplified difference between the coil voltages, is fed to the amplifier U3. Resistors R16 and R17 determine the gain of this stage, which functions as a rectifier network. The diodes D3 and D4 determine that the amplified output voltage from this stage is always positive. The output signal from this stage is integrated by capacitor C18, which has an additional discharge path through resistor R18 to reset more quickly the display lights when there is a reduced voltage output from U3.

The output of amplifier U3 which is a positive rectified d.c. signal after capacitor C18, is then fed to non-inverting amplifier U4. A negative d.c. voltage from resistor R20, which is filtered by capacitor C19, is summed with the amplifier U3 output before amplifier U4 giving a net voltage close to zero volts for a no-metal-detected state. This summing serves to eliminate any voltage due to the natural imbalance of the receive coils. Resistors R22, R23 and R24 determine gain.

The output from amplifier U4 is fed to the display driver U5. Depending upon the level of that output, one of the L.E.D.s D5–D14 will illuminate. These are set to light sequentially as the output from U4 increases from a minimum to a maximum.

At the same time, the speaker circuit is activated, assuming a voltage output from amplifier U4. This circuit is an R-C unijunction-type oscillator which, as the output from U4 varies, so does the charging current to capacitor C12 and the frequency of the tone of the speaker will rise with increasing voltage signifying increasing proximity to the metal band.

The low voltage battery circuit works as follows. As long as the battery voltage is above the sum of the voltage drop across resistor R30 plus the zener diode voltage plus Vbe of Q4, the transistor Q4 stays on and Q5 is off. If the battery voltage drops, Q4 turns off and Q5 turns on, lighting L.E.D. D15.

It should also be noted that V+ is supplied to the amplfiers in the preferred embodiment by decoupling it from the positive supply by resistor R6 and capacitor C5. Likewise, resistor R8 and capacitor C10 decouple the V− from conventional voltage doubler circuit 54.

OTHER EMBODIMENTS

Figure 5:
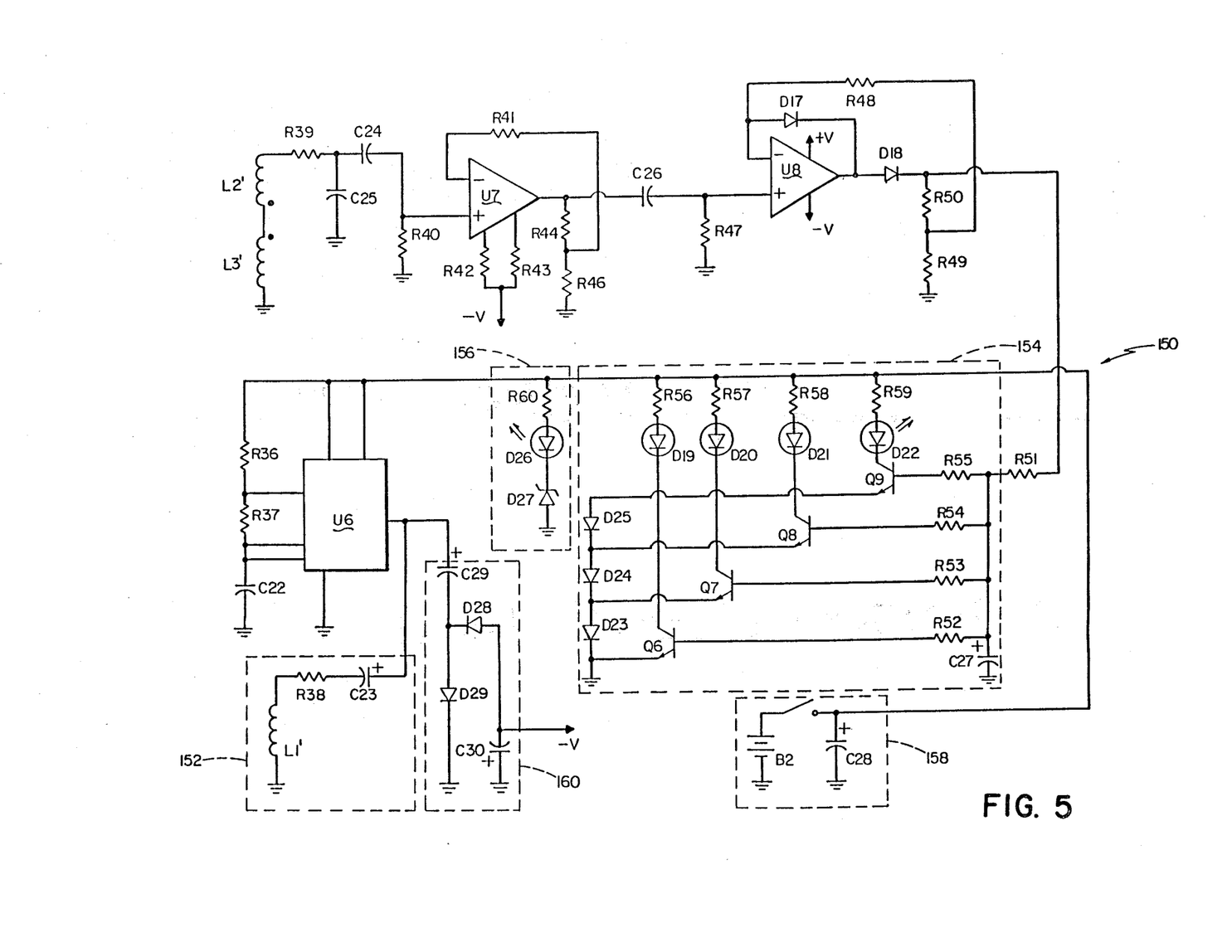
FIG. 5 is a schematic diagram of another circuit of this invention.

Referring to FIG. 5, another circuit for the instrument 30 is shown at 150.

An oscillator U6, having resistors R36, R37 and capacitor C22 as an input stage, produces an alternating output current which is fed to a transmit coil circuit 152. Oscillator U6 is an NE555, and resistors R36, R37 are 10K ohms and 330K ohms respectively. Capacitor C22 is 0.0018 microfarads.

Transmit coil circuit 152 comprises capacitor C23 in series with resistor R38 and transmitting coil L1'. Oscillator U6, which draws about 10-12 milliamps, provides an output signal with sufficient output current capability to drive transmitting coil L1' which produces a magnetic field as in the preferred embodiment.

Also as in the preferred embodiment, two receiving coils L2' and L3' are within the magnetic field when the circuit 152 is activated. Receiving coils L2' and L3', however, are connected in the polarity shown so that the net voltage output from the combination will be the difference in the voltage dropped across each coil. This net voltage output is sent through resistor R39 and capacitor C24 to the positive input of a non-inverting amplifier U7. Capacitor C25 and resistor R40 are separately connected between this input line and ground. The amplifier U7 is an LM747. Resistors R39 and R40 are 10K ohms and 100K ohms respectively. Capacitors C24 and C25 are 0.0068 microfarads and 0.015 microfarads.

The feedback loop for amplifier U7 has resistors R41 and R44, both being 100K ohms. Resistor R46 and 100 ohms is connected between the loop and ground. Offset resistors R42, R43 are selected so that the output from amplifier U7 will be zero if the voltage across the coils L2' and L3' are equal. The sum of the resistors R42 and R43 is about 100K ohms for this embodiment.

The a.c. output voltage (if any) from the amplifier U7 is fed through capacitor C26 to the positive input for amplifier U8. As in the preferred embodiment, the magnitude of this signal depends upon the amount of difference in the voltages across the receiving coils, and that is dependent upon any increase in flux density through coil L2' due to the proximity of the metal band.

Amplifier U8 and its circuitry act as a precision rectifier. Diode D17 is connected between the output and the negative input of amplifier U8. Resistors R48 and R50 in series are connected between the negative input of amplifier U8 and through diode D18 to the amplifier output. Diodes D17, D18 are 1N4009. Resistors R48, R50 are 100K ohms and 10K ohms respectively. Also, resistors R47 and R49 are connected to ground as shown. These resistors are 100K ohms and 330 ohms respectively.

The d.c. voltage output (if any) from the amplifier circuit is fed through resistor R51 of 100 ohms to the display circuit 154. Display circuit 154 comprises four L.E.D. circuits, one each for L.E.D.s D19, D20, D21 and D22. Referring to the circuit for LED D19, the d.c. voltage from the amplifier U8 is fed through resistor R52 to the base of transistor Q6, thereby turning it on. A current flows through the transistor and D19 and resistor R56 causing L.E.D. D19 to light. D20 lights in the same manner, except that due to the presence of diode D23 in its L.E.D. circuit, the voltage on the base of transistor Q7 must be somewhat higher to create a current flow through diode D20. Diode 21 requires still more transistor base voltage for Q8 as its circuit has two diodes in it, diodes D24 and D23. Similarly, still more voltage is required for the three diode circuit of L.E.D. D22. The net effect is that the L.E.D.s light in sequence, but unlike the preferred embodiment, all will be on for a maximum voltage condition (i.e., close proximity of the coil L2' to the metal band). Transistors Q6-9 are all 2N5734. Resistor R52 is 1.8K ohms. Resistors R53 and 54 are both 1K ohms, and resistor R55 is 680 ohms. The diodes D23, 24, 25 are all 1N4009. Resistors R56, 57 are 470 ohms. Resistor R58 is 330 ohms and resistor R59 is 220 ohms. Filter capacitor C27 is 47 microfarads.

A circuit 156 comprised of resistor R60 in series with L.E.D. D26 and zener diode 027 is connected between the +V and ground. While the +V level is sufficient, L.E.D. D26 will light. Resistor R60 is 220 ohms and the zener diode is a 4.7 volt diode.

Battery circuit 158 provides the +V voltage. Battery circuit 158 has a 9 volt battery B2, a switch SW2 and a filter capacitor C28 of 68 microfarads.

The −V voltage is provided by doubler circuit 160, which is similar to the doubler circuit 54 of the preferred embodiment. Here, capacitor C29 is 22 microfarads and capacitor C30 is 47 microfarads. The diodes D28, D29 are 1N192.

Figure 6:
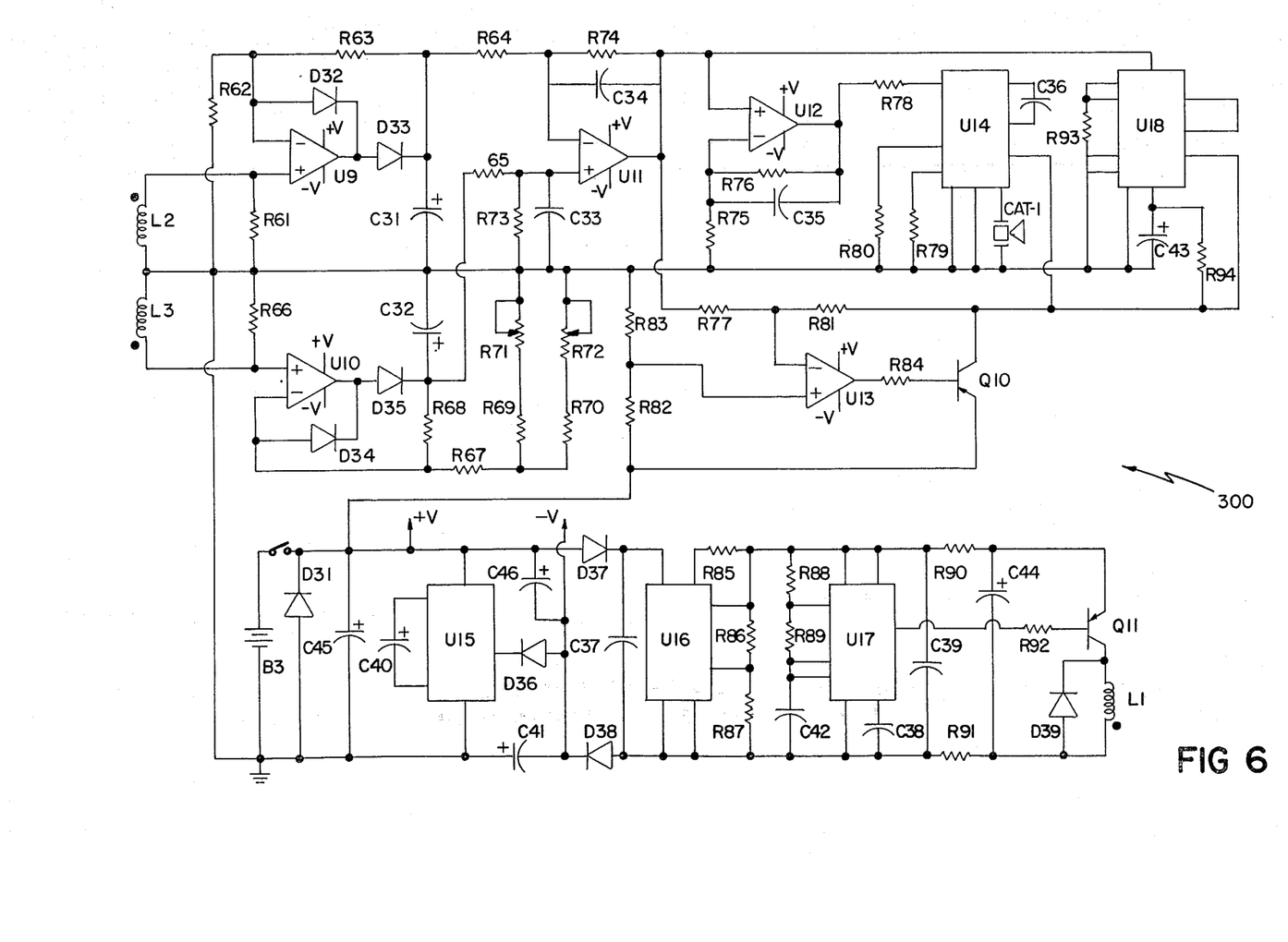
FIG. 6 is a schematic diagram of the preferred circuit of this invention.

Referring to FIG. 6, the presently preferred circuit is shown at 300. A voltage source B3 is connected between ground and a switch (actually corresponding to switch SW1 in FIG. 1). The voltage source B3 is preferrably a 9 volt battery, although other sources may be used. Diode D31, an 1N4001, is connected across voltage source B3 to prevent circuit damage if the voltage source is inadvertently connected with polarity reversed from that shown. Capacitor C45, which is connected across diode D31, acts as a noise filter. Capacitor C45 is 68 microfarads.

A negative voltage convertor, integrated circuit U15, is connected across the voltage source B3 and the switch. Capacitors C40 and C41 and diode D36 comprise a charge pump for converter U15, which efficiently converts the supply voltage from source B3 from positive to negative on the line designated −V. This line is connected to the other devices of the circuit requiring negative voltage, and capacitor C46 acts as a filter between the −V and +V lines, the latter tapped upstream from convertor U15.

A pair of diodes D37, D38 are located downstream from the converter U15, and the diodes reduce the voltage applied to the rest of transmitter circuitry associated with a central coil (designated L1 in this embodiment as in the previous embodiment). Diodes D37, 38 are both 1N4148As. Immediately downstream from the diodes D37, D38 is a monolithic voltage regulator U16, which uses resistor R85 as a current sensor and which provides a constant voltage to the remainder of the L1 transmitter circuitry. Accordingly, as the voltage source B3 ages, and its output falls somewhat, the voltage to the rest of the L1 circuit remains constant. Resistors R86 and R87 determine the actual output voltage of voltage regulator U16. Regulator U16 is a Intersil ICL7663, and resistors R86 and 87 are 680K ohms and 100K ohms, respectively. Resistor R85 is 100 ohms.

The regulator U16 supplies voltage to astable multivibrator U17, the frequency and duty cycle of which are controlled by resistors R88 and R89 and capacitor C42. Capacitor C38 filters an internal reference point in multivibrator U17 and capacitor C39 filters the supply voltage to multivibrator U17. Multivibrator U17 is an Intersil ICM7555. Resistors R88 and 89 are 33K ohms and 1K ohms respectively, while C42 is 0.01 microfarads. Capacitors C38 and C39 are both 0.1 microfarads. With the associated elements having these values, the pulses from multivibrator U17 are 8 microseconds in duration at 4 KHz. Of course, different timing may be used by varying the multivibrator type or the values of the resistors or capacitors.

Resistors R90 and R91 along with capacitor C44 decouple transistor Q11 from the rest of the circuitry. Resistors R90 and 91 are both 270 ohms, and capacitor C44 is 22 microfarads. Transistor Q11 is a 2N2907A.

Capacitor C44 also acts as a reservoir in that when the transistor Q11 turns on, and there is a current flow through coil L1, which is connected to the collector of the transistor Q11, the voltage provided by regulator U16 does not decrease appreciably. Base current to the transistor Q11 is provided from multivibrator U17 through resistor R92, 1K ohms. The combination of the multivibrator U17 and transistor Q11 provide a great deal of energy to the coil, while drawing relatively little battery current. Diode D39, and 1N4148A, which is across coil L1, clamps any transient voltages generated by the coil L1 when transistor Q11 turns off. In this configuration, the peak current through coil L1 is about 60 milliamps.

The outer and inner coils L2, L3 are each connected to a separate input amplifier circuit, which are very similar, but not identical. Coil L2 is connected to the positive input for amplifier U9. The gain of amplified U9 is set by resistors R62 and R63, and the gain is fixed. Diodes D32 and D33 are connected to the amplifier U9 to assure that the amplifier output is always positive. Resistor R61 is a terminating resistor connected between the positive input of the amplifier U9 and the other side of coil L2. Amplifier U9 is a Texas Instruments TL081. Resistors R62 and R63 are 5.1K ohms and 100K ohms respectively, and the diodes D32 and D33 are both 1N4148As. Resistor R61 is 270 ohms.

The amplifier circuit for coil L3 is comprised of amplifier U10, the positive input of which is connected to coil L3. Diodes D34 and D35 and terminating resistor R66 are connected in the same manner as with the amplifier circuit for coil L2. The gain of this amplifier circuit, however, is variable and controlled by two parallel, variable resistors R71 and R72, which are connected in series to resistors R69 and R70 respectively. Resistors R67 and R68 are also connected between the resistors R69 and R70 and the rest of the amplifier circuit. Amplifier U10 is the same type as amplifier U9. Diodes D34 and D35 are both 1N4148As. Terminating resistor R66 is 270 ohms, and variable resistors R71 and R72 are 1K ohms and 5K ohms respectively. Resistor R71 is the coarse adjustment, and resistor R72 is the fine adjustment. Resistors R67 and R68 are 3.9K ohms and 100K ohms respectively.

The amplified output pulses, which are mostly positive going pulses from the amplifier circuits are integrated to d.c. by capacitors C31 and C32 and are then fed to a differential amplifier circuit. Amplifier U11 and resistors R64, R65, R73 and R74 along with capacitors C31 and C32, which limit bandwidth, comprise this differential amplifier circuit, the output of which is fed to comparator U13. Amplifier U11 is a PMI OP20, while resistors R64 and R65 are both 10K ohms. Resistors R73 and R74 are both 1M ohms, and capacitors C33 and C34 are 0.01 microfarads.

Initially, inherent coil differences may result in a small difference in the voltages across capacitors C31 and C32, both 6.8 microfarads.

Thus, the unit must be calibrated prior to use to compensate and elminate that difference. For calibration of the instrument, the output of amplifier U11 must be adjusted to zero volts when the fields from the coils are not disturbed by the presence of metal. The output of amplifier U11 is monitored as resistors R71 and 72 are varied to obtain a zero voltage reading. Generally, this is accomplished by setting resistor R72 to its midpoint, and then turning resistor R71 until there is a zero output from amplifier U11.

In actual operation, the output of amplifier U11 is fed to comparator U13. Comparator U13 in turn, through resistor R84, controls the operation of transistor Q10, which acts as a switch. Resistors R77 and R81 provide hysteresis. Generally, if the output voltage from amplifier U11 is below a value determined by resistors R82 and R83, the comparator U13 will not turn on the transistor Q10. If the voltage from amplifier U11 is large enough, comparator U13 will turn on transistor Q10, which will then conduct, and the supply voltage will be applied to the later stages (audio and display stages to be discussed below) of the circuit. This arrangement means that battery power is supplied to the later stages only when the presence of metal is detected instead of constantly, thereby increasing battery life. Comparator U13 is a PMI OP20. Resistor R84 is 20K ohms, and transistor Q10 is a 2N2907A. Resistors R82 and R83 are 100K ohms and 1K ohms respectively, and resistors R77 and R81 are 20K ohms and 3.3M ohms respectively.

The output from amplifier U11 is also fed to the positive input of amplifier U12, which is configured as a non-inverting amplifier. Resistors R75 and R76 as well as capacitor C35 are part of that circuit, whereby the resistors determine the gain while the capacitor limits the bandwidth. Amplifier U12 is an PMI OP20, and capacitor C35 is 0.1 microfarads. Resistors R75 and R76 are 20K ohms and 100K ohms respectively.

The non-inverting amplifier circuit feeds its signal to an audio circuit which is primarily comprised of a voltage controlled oscillator U14 and a piezo ceramic audio transducer CAT-1. The control voltage to the oscillator U14 is provided through resistor R78. Resistors R79 and R80 and capacitor C36 determine the operating frequency range and the offset for the voltage controlled oscillator U14. When there is a sufficient signal at the output of amplifier U12, the transducer CAT-1 will sound an audible alarm, the intensity and frequency of which increases proportionately with the magnitude of the signal up to a certain selected limit. The oscillator is the voltage controlled oscillator portion of a RCA CD4046, and resistor 78 is 5.1K ohms. Resistors R79 and R80 are 47K ohms and 470K ohms respectively, and capacitor C36 is 0.01 microfarads.

A visual display circuit comprises a multi L.E.D. display U18. Resistor R93 determines the L.E.D. brightness, and resistor R94 decreases power dissipation. Capacitor C43 filters transients resulting from the switching action of the L.E.Ds. Display U18 is a National Semiconductor NSM3914. Resistors R93 and R94 are 270 ohms and 180 ohms respectively, and capacitor C43 is 39 microfarads.

Another variation of the invention is in the arrangement of the coils L1, L2 and L3. As shown in FIGS. 2 and 3 the coils are arranged axially in line. The coils, however, can be arranged in a planar arrangement whereby each coil is in line but in the same plane, (such as three donuts lying on a tray in a straight line). A triangular planar arrangement is also possible. These additional arrangements create a more extensive field in one direction (rather than a uniform field in all directions) and detection is enhanced.

Other uses and variations are possible. For example, in addition to use with endotracheal tubes, the method and apparatus of this invention can also be used with other medical devices, such as stomach tubes, tracheal tubes, venus catheters, arterial catheters, surgical sponges, and other types of catheters and devices, the position of which in tissue is important. Further, other fields e.g., electrical fields with a dielectric instead of a metal band on the tube, can be used in place of the magnetic field and the metal band.

Other variations will occur to those skilled in the art. What I claim is:

1. A circuit for determining very accurately the position of a device in biological tissue, comprising:
    a detector means,
        said detector means having a field coil which, when activated, generates a field, said detector means also having a first receiving coil and a second receiving coil which are both disposed in the field generated by said field coil,
        said first receiving coil producing a first a.c. output signal and said second receiving coil producing a second a.c. output signal when the field is generated, and
    an alarm means,
        said alarm means having a first rectifier means and a first integrator means, said first rectifier means receiving the first a.c. output signal and converting it to a first d.c. signal and said first integrator means converting the first d.c. signal to a first d.c. averaged signal,
        said alarm means also having a second rectifier means and a second integrator means, said second rectifier means being an active rectifier having an amplifier means and a means for adjusting the output of said amplifier means, said second rectifier means receiving the second a.c. output signal and converting it to a second d.c. signal, the amplitude of which may be varied by said means for adjusting, and said second integrator means converting the second d.c. signal to a second d.c. averaged signal, the amplitude of the second d.c. averaged signal being adjusted by said means for adjusting to be identical with the first d.c. averaged signal when the device is not detected,
        said alarm means further including an alarm amplifier means which receives the first and second d.c. average signals and produces an alarm output corresponding to any difference between them, as would be caused by the presence of the device inside the field, whereby the alarm output is used to activate an alarm.

2. The circuit of claim 1 wherein said alarm amplifier means is a differential amplifier and the alarm output of which is a high gain output when the device is in the field and zero when the field is not disturbed by the presence of the device.

3. The circuit of claim 1 wherein said means for adjusting the output of said amplifier means of said second rectifier means is at least one variable resistor.

4. The circuit of claim 1 wherein said alarm is an audio circuit which receives the alarm output and is activated thereby, when the alarm output is other than zero.

5. The circuit of claim 4 wherein a non-inverting amplifier is connected between said alarm amplifier means and said audio circuit, said non-inverting amplifier receiving the alarm output and sending an output which is based on the alarm output to said audio circuit.

6. The circuit of claim 4 wherein said audio circuit comprises a voltage controlled oscillator which receives and is driven by the voltage of the alarm output and which in turn drives an audio transducer with its output.

7. The circuit of claim 4 further comprising a voltage comparator and a switch means, said comparator receiving the alarm output from said alarm amplifier means and activating said switch to provide voltage to said audio circuit if the alarm output is of or greater than a predetermined magnitude.

8. The circuit of claim 7 wherein said switch means is a transistor, the base current for which is provided by said voltage comparator.

9. The circuit of claim 1 further comprising a visual display circuit which revievs the alarm output from said alarm amplifier means.

10. The circuit of claim 9 wherein said display circuit comprises a signal display module having a plurality of L.E.D.s.

11. The circuit of claim 9 further comprising a voltage comparator and a switch means, said comparator receiving the alarm output from said alarm amplifier and activating said switch to provide voltage to said visual display circuit if the alarm output is of or greater than a predetermined magnitude.

12. The circuit of claim 1 wherein said field coil is driven by a voltage regulator.

13. The circuit of claim 12 wherein said voltage regulator includes an astable multivibrator which provides pulses to a transistor switch feeding said field coil.

14. The circuit of claim 1 further comprising a voltage source which is connected to a negative voltage converter and which provides negative voltage to said circuit.

* * * * *